United States Patent
Allef et al.

(10) Patent No.: US 9,956,433 B2
(45) Date of Patent: *May 1, 2018

(54) FOAMABLE OIL-WATER EMULSION

(71) Applicant: DEB IP LIMITED, Denby (GB)

(72) Inventors: Petra Allef, Essen (DE); Marcel Veeger, Goch (DE); Volker Klotzbach, Wachtendonk (DE)

(73) Assignee: DEB IP LIMITED, Denby, Derbyshire (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/716,464

(22) Filed: May 19, 2015

(65) Prior Publication Data
US 2015/0250722 A1   Sep. 10, 2015

Related U.S. Application Data

(63) Continuation of application No. 13/380,064, filed as application No. PCT/EP2010/059246 on Jun. 30, 2010, now Pat. No. 9,132,292.

(30) Foreign Application Priority Data

Jul. 31, 2009  (DE) ........................ 10 2009 028 156

(51) Int. Cl.
| | |
|---|---|
| *A61Q 19/00* | (2006.01) |
| *A61K 8/06* | (2006.01) |
| *A61K 8/04* | (2006.01) |
| *A61K 9/00* | (2006.01) |
| *A61K 9/107* | (2006.01) |
| *A61K 8/34* | (2006.01) |
| *A61K 8/37* | (2006.01) |
| *A61K 8/92* | (2006.01) |
| *A61K 8/97* | (2017.01) |
| *A61K 9/12* | (2006.01) |
| *A61K 47/10* | (2017.01) |
| *C11D 1/10* | (2006.01) |
| *A61K 47/14* | (2017.01) |
| *A61K 47/44* | (2017.01) |
| *A61K 47/46* | (2006.01) |
| *A61Q 1/14* | (2006.01) |
| *A61Q 17/04* | (2006.01) |
| *A61Q 19/10* | (2006.01) |
| *C11D 3/00* | (2006.01) |
| *C11D 3/20* | (2006.01) |
| *C11D 3/382* | (2006.01) |

(52) U.S. Cl.
CPC .............. *A61Q 19/00* (2013.01); *A61K 8/046* (2013.01); *A61K 8/062* (2013.01); *A61K 8/068* (2013.01); *A61K 8/34* (2013.01); *A61K 8/37* (2013.01); *A61K 8/922* (2013.01); *A61K 8/97* (2013.01); *A61K 9/0014* (2013.01); *A61K 9/107* (2013.01); *A61K 9/122* (2013.01); *A61K 47/10* (2013.01); *A61K 47/14* (2013.01); *A61K 47/44* (2013.01); *A61K 47/46* (2013.01); *A61Q 1/14* (2013.01); *A61Q 17/04* (2013.01); *A61Q 19/10* (2013.01); *C11D 1/10* (2013.01); *C11D 3/0094* (2013.01); *C11D 3/2068* (2013.01); *C11D 3/2093* (2013.01); *C11D 3/382* (2013.01); *A61K 8/92* (2013.01); *A61K 2800/592* (2013.01); *A61K 2800/596* (2013.01)

(58) Field of Classification Search
CPC .......... A61K 8/062; A61K 8/046; A61K 8/92; A61K 8/37; A61K 2800/596; A61K 47/14; A61K 47/44; A61K 8/922; A61K 9/0014; A61K 9/107; A61K 9/122; A61Q 17/04; A61Q 19/00; C11D 1/10; C11D 3/0094

See application file for complete search history.

(56) References Cited

U.S. PATENT DOCUMENTS

| | | | |
|---|---|---|---|
| 5,500,211 | A | 3/1996 | George et al. |
| 6,231,844 | B1 | 5/2001 | Nambu |

(Continued)

FOREIGN PATENT DOCUMENTS

| | | |
|---|---|---|
| AT | 501699 A1 * | 10/2006 |
| DE | 102 50 755 A1 | 5/2004 |

(Continued)

OTHER PUBLICATIONS

Merz Pharma, AT 501699 A1 (Oct. 2006), Espacenet English Translation, downloaded Feb. 2017.*

(Continued)

*Primary Examiner* — Mark V Stevens
(74) *Attorney, Agent, or Firm* — Grüneberg and Myers PLLC

(57) ABSTRACT

The present invention relates to foamable oil-in-water emulsions containing: A) one or more emulsifiers, at least one of which is a non-ionic emulsifier, B) one or more cotensides, C) one or more oils, D) optionally, one or more polar solubilizers, E) optionally, auxiliary and additive substances, F) one or more surfactants, G) water, H) optionally, water-soluble substances, provided that the water content of the emulsion is ≥70% by weight and the concentration of surfactant(s) F) is from 0.01 to less than 10% by weight, each based on the entire emulsion. The invention further relates to a method for producing the oil-water emulsions according to the invention, to foams obtained from these oil-water emulsions, to a method for producing the foams, and to the application of the oil-water emulsions according to the invention and to the foams produced therefrom.

14 Claims, No Drawings

(56) References Cited

U.S. PATENT DOCUMENTS

| | | |
|---|---|---|
| 6,541,016 B1 | 4/2003 | Turowski-Wanke et al. |
| 7,173,086 B2 | 2/2007 | Smith et al. |
| 7,777,093 B2 | 8/2010 | Smith et al. |
| 7,842,386 B2 | 11/2010 | Loeker et al. |
| 8,288,002 B2 | 10/2012 | Loeker et al. |
| 8,466,097 B2 | 6/2013 | Allef et al. |
| 8,491,920 B2 | 7/2013 | Veeger et al. |
| 8,518,541 B2 | 8/2013 | Loeker et al. |
| 2005/0187121 A1 | 8/2005 | Dietz |
| 2005/0271598 A1* | 12/2005 | Friedman ............ A61K 8/046 424/47 |
| 2007/0178144 A1* | 8/2007 | Hameyer ............ A61K 8/062 424/443 |
| 2008/0009616 A1 | 1/2008 | Frank et al. |
| 2008/0138296 A1 | 6/2008 | Tamarkin et al. |
| 2010/0075844 A1 | 3/2010 | Loeker et al. |
| 2010/0279860 A1 | 11/2010 | Smith et al. |
| 2011/0009272 A1 | 1/2011 | Wattebled et al. |
| 2011/0206623 A1 | 8/2011 | Wenk et al. |
| 2012/0001122 A1 | 1/2012 | Wattebled et al. |
| 2012/0101060 A1 | 4/2012 | Thoerner et al. |
| 2012/0302445 A1 | 11/2012 | Rudolph et al. |

FOREIGN PATENT DOCUMENTS

| | | |
|---|---|---|
| DE | 10 2004 016 710 A1 | 10/2005 |
| EP | 1388338 A1 | 2/2004 |

OTHER PUBLICATIONS

International Search Report (English Translation), dated Mar. 7, 2012, 3 pages.

International Preliminary Report on Patentability (English Translation), dated May 30, 2012, 14 pages.

\* cited by examiner

FOAMABLE OIL-WATER EMULSION

The present invention relates to a foamable O/W emulsion and to its use for producing care foam, in particular a skin care foam.

Cosmetic products in the form of foams enjoy great popularity, particularly in the USA. For reasons of environmental protection, such foams should nowadays be produced wherever possible without classic propellant gases, but using air. Corresponding containers which have a suitable foaming device are sold e.g. by Airspray, recently part of REXAM PLC. The foams are used e.g. in hairstyling products, in foaming products for face and body cleansing and also as foamable emulsions.

DE 10 2004 051 420 describes propellant-gas-free foam-forming systems which comprise a carbohydrate surfactant, in particular sugar ester or sugar ether, and are capable of foam formation without propellants. These aqueous systems preferably comprise alcohols, in particular ethanol.

DE 100 58 224 (Henkel) describes propellant-gas-free spray preparations which comprise microemulsions with a droplet size of below 500 nm. A suitability for producing foam creams is not described.

In recent times, microemulsions have been used for producing foamable formulations. For example, US 2006/0217283 (L'Oréal) describes foam compositions in the form of oil-in-water (O/W) emulsions. These emulsions have the oil phase in the form of droplets with a size of less than or equal to 4 µm. The fraction of oil phase in the emulsion is more than 30% by mass. The emulsion has an emulsifier system and also foam surfactants. The mass ratio of oil phase to foam surfactants is 1.5 to 12. The emulsions are preferably produced by the phase inversion temperature method. The foam surfactants used are preferably mixtures which have alkyl polyglycosides and amphoteric surfactants, such as e.g. betaines. As emulsifier systems, preference is given to those which have ethoxylated fatty alcohols or fatty acids, or consist of these.

The commercially available systems capable of foam formation often have the disadvantage that they do not have long term stability and therefore separate into oil phase and water phase. Consequently, these systems must first be shaken prior to use. However, such shaking is usually impossible in the case of products which from dispensers which are attached to walls or other objects.

Dr. Klaus Kwetkat describes in "Formulation of homogeneous O/W emulsion pump foams", Speciality Chemicals Magazine, November 2005, pages 38 and 39, the production of stable foams which can be used as leave-on emulsion mousse. However, reworkings of the stated formulations have revealed that these formulations too do not have long term stability, phase separation thus occurring over a period of 3 months at 40° C.

It was therefore an object of the present invention to provide a foamable composition which does not comprise a propellant gas, which remains stable even over a prolonged period and thus can also be used in fixedly installed foaming devices. The foam obtained should preferably be stable or at least largely stable for the duration of application break upon rubbing on the skin. Moreover, the emulsion should absorb as quickly as possible into the skin.

Surprisingly, it has been found that O/W emulsions which are based on microemulsions, as are described e.g. in DE 10 2006 004 353 or DE 195 14 269, and which have from 0.01 to less than 10% by mass of a (foam) surfactant and greater than or equal to 70% by mass of water, are stable for 3 months at 40° C. In particular, it is surprising that, despite using a comparatively small amount of surfactant, it is possible to produce stable foam without using synthetic propellants. Within the context of the present invention, stable foams are understood as meaning foams which is completely filled in a 25 ml beaker of height 5 cm by 10 pump strokes à 0.4 g (e.g. Elegant Foamer Line M3 foam dispenser from Rexam Airspray) and this resulting foam does not collapse to a foam height of 2.5 cm (50%) within 3 min.

The present invention therefore provides a foamable oil-in-water emulsion comprising:
A) one or more emulsifiers, where at least one nonionic emulsifier is present,
B) one or more cosurfactants,
C) one or more oils,
D) optionally one or more polar solubilizers,
E) optionally auxiliaries and additives,
F) one or more surfactants,
G) water,
H) optionally water-soluble substances,
with the proviso that the water content of the emulsion is ≥70% by weight and the content of surfactant(s) (F) is from 0.01 to less than 10% by weight, based on the total emulsion.

Moreover, the present invention provides a method for producing the O/W emulsions according to the invention, foams obtainable from these O/W emulsions, a method for producing the foams and also the use of the O/W emulsions according to the invention and/or of the foams produced therefrom, as described in the claims and hereinbelow.

The foamable O/W emulsions according to the invention have the advantage that they are stable over a prolonged period, at least for 3 months. In this connection, long term stability is understood as meaning that the emulsions according to the invention can be stored for 3 months at room temperature, 4° C. and 40° C. without irreversible creaming or other signs of instability such as e.g. separation of the phases. The foamability does not change over this period, i.e. foams of comparable quality are obtained.

The stability of the O/W emulsions according to the invention makes it possible to also use these emulsions in foamers which are fixedly installed and in which shaking prior to application is therefore impossible. The stability furthermore has the advantage that it is possible to dispense with mechanical aids in the foaming apparatus for the purposes of homogenization prior to application. The foaming apparatus can therefore simply consist of a storage container for the O/W emulsion and the actual foaming/application device.

Moreover, the foamable O/W emulsions according to the invention have the advantage that they can be produced without the use of synthetic propellant gases, in particular without the use of organic, often flammable or environmentally harmful propellant gases.

A further advantage of the O/W emulsions according to the invention is that a very small amount of surfactants is required in order to ensure foamability. Since surfactants can often adversely affect the skin compatibility of products, the risk of skin incompatibility of the foams produced from the O/W emulsion according to the invention is reduced.

A further advantage of the O/W emulsions according to the invention is that they can be produced free from ethoxylated constituents. This too leads to better skin compatibility.

The foams produced from the O/W emulsion according to the invention, in particular cream foams, have the advantage that the emulsion, following application of the foam to the skin and after breaking the foam on the skin, very rapidly absorbs and thus produces a pleasant skin feel. The cream foams according to the invention are thus lighter and absorb more quickly into the skin than conventional creams.

The present invention is described below by way of example without any intention to restrict the invention to these exemplary embodiments. Where ranges, general formulae or compound classes are given below, then these are intended to include not only the corresponding ranges or groups of compounds that are explicitly mentioned, but also all part ranges and part groups of compounds which can be obtained by removing individual values (ranges) or compounds. If documents are cited within the course of the present description, then their content should, in its entirety, be deemed as forming part of the disclosure of the present invention. Unless stated otherwise, all percentage data below are data in mass percent and all average value data are number-average data.

The foamable oil-in-water emulsions according to the invention are characterized in that they comprise
- A) one or more emulsifiers, where at least one nonionic emulsifier is present,
- B) one or more cosurfactants,
- C) one or more oils,
- D) optionally one or more polar solubilizers,
- E) optionally auxiliaries and additives,
- F) one or more surfactants, in particular foam surfactants, in particular those foam surfactants which aid the production of foams without the use of synthetic, in particular organic, propellants,
- G) water,
- H) optionally water-soluble substances, which preferably do not fall under components A to F, such as e.g. active ingredients, such as e.g. gingko *biloba* extract, panthenol, creatine or allantoin, with the proviso that the water content and preferably the water phase content of the emulsion is ≥70% by weight, preferably from ≥80 to ≤99% by weight, preferably 90 to 97.5% by weight and particularly preferably from 92.5 to 95.0% by weight, and the content of surfactant(s) (F) is from 0.01 to less than 10% by weight, based on total emulsion. Included in the water phase here are all substances of a formulation which, on account of their hydrophilic character, can be admixed to this phase and/or be dissolved or dispersed therein. Thus, based on the oil-in-water emulsions according to the invention, in each case water and any constituents such as glycols, polyalkylene glycols, glycerol, polyglycerols, alcohols, water-soluble polymers or active ingredients form part of the water phase.

The average particle size (diameter) of the dispersed oil phase is preferably less than or equal to 4 µm, preferably from 20 to 1000 nm, particularly preferably from 30 to 250 nm. The determination of the average particle size can take place as described in DE 10 2006 004 353 by dynamic light scattering.

The O/W emulsions according to the invention are preferably of low viscosity. Within the context of the present invention, of low viscosity is understood as meaning a viscosity of ≤4000 mPas (determined with Brookfield RVT, Spindle 2, 20 rpm (20° C.)), preferably ≤2500 mPas, particularly preferably from 100 to 2000 mPas. Higher viscosities can be established, but are not preferred according to the invention. As a result of low viscosity, good foamability can be achieved in standard commercial foamers.

In the oil-in-water emulsion according to the invention, the emulsifiers A), the cosurfactants B) and the oils C) are present preferably in mass fractions (based on these three components) of from ≥10 to ≤30 (A), ≥3 to ≤20 (B) and ≥50 to ≤87 (C), preferably in mass fractions of ≥20 to ≤25 A)/≥5 to ≤15 B)/≥60 to ≤75 C).

Nonionic emulsifiers A) which may be present are all nonionic emulsifiers, in particular the nonionic emulsifiers specified in DE 100 58 224 or DE 195 14 269. Preferred nonionic emulsifiers A) are those as specified below as emulsifiers a).

It may be advantageous if, as emulsifiers A), an emulsifier mixture A1) consisting of: a) at least one nonionic primary emulsifier and b) at least one secondary emulsifier containing one or more acid functions and whose acid function can optionally be completely or partially neutralized, are present.

In the emulsifier mixture A1), the nonionic primary emulsifiers a) preferably present are one or more polyol partial esters selected from at least one of the groups:
- a1) glycerol and polyglycerol partial esters, preferably produced by esterification of aliphatic, linear or branched, optionally unsaturated and/or hydroxyfunctionalized carboxylic acids with a chain length of ≥6 to ≤22 carbon atoms with glycerol, polyglycerols or mixtures of the two,
- a2) sorbitan or sorbitol partial esters, preferably produced by esterification of aliphatic, linear or branched, optionally unsaturated and/or hydroxyfunctionalized carboxylic acids with a chain length of ≥6 to ≤22 carbon atoms with sorbitol,
- a3) carbohydrate esters, preferably glycoside or sucrose esters, preferably produced by esterification of aliphatic, linear or branched, optionally unsaturated and/or hydroxyfunctionalized carboxylic acids with a chain length of ≥6 to ≤22 carbon atoms with mono- or polysaccharides, and also optionally moreover, or
- a4) (alkyl poly)glycosides, preferably produced by reaction of aliphatic, linear or branched, optionally unsaturated and/or additionally hydroxyfunctionalized alcohols with a chain length of ≥6 to ≤22 carbon atoms with mono- or polysaccharides, or mixtures thereof.

Preferably, the main part of the nonionic primary emulsifier component a) consists of polyglycerol esters a1) in an amount of ≥25 to <100% by weight, preferably ≥50 to <100% by weight, particularly preferably ≥75 to <100% by weight, to which preferably sorbitan esters a2) are admixed in an amount of >0 to ≤75% by weight, preferably >0 to ≤50% by weight, particularly preferably >0 to ≤25% by weight, based on the total primary emulsifier component a). Preference is given here to polyglycerol and sorbitan partial esters which preferably contain, as hydrophobic fractions, in each case fatty acid radicals with a chain length of ≥10 to ≤18 carbon atoms. Very particularly preferably, the primary nonionic emulsifier component a) comprises a combination of polyglycerol laurates and sorbitan laurates, or consists preferably of these.

The emulsifier mixture (A1) comprises, as secondary emulsifier component (b), preferably one or more compounds selected from at least one of the groups:
- b1) optionally hydroxyl-group-containing di- or polycarboxylates, preferably sulfated, sulfonated or phosphated carboxylates, malonates, malates, succinates, sulfosuccinates, citrates, tartrates, in which the acid groups have preferably been partially esterified with aliphatic or aromatic, linear or branched, optionally unsaturated and/or hydroxyfunctionalized alcohols with a chain length of ≥6 to ≤22 carbon atoms,
- b2) optionally hydroxyl-group-containing di- or polycarboxylates, preferably sulfated or sulfonated or phosphated carboxylates, malonates, malates, succinates, sulfosuccinates, citrates, tartrates, in which the acid groups have preferably been partially esterified with polyols, polyol partial esters, preferably of glycerol, polyglycerol and/or sorbitol with aliphatic or aromatic, linear or branched, optionally unsaturated and/or hydroxyfunctionalized carboxylic acids with a chain length of $\geq 6$ to $\leq 22$ carbon atoms, b3) polyols, preferably glycerol, polyglycerol and sorbitol, which have preferably been partially esterified with aliphatic or aromatic, linear or branched, optionally unsaturated and/or hydroxyfunctionalized mono-, di- or polycarboxylic acids with a chain length of $\geq 2$ to $\leq 22$ carbon atoms, with the proviso that free, neutralizable acid groups are present in the molecule, b4) hydroxyfunctional mono-, di- or polycarboxylic acids, the hydroxyl groups of which have preferably been reacted at least partially with aliphatic, linear or branched, optionally unsaturated and/or hydroxyfunctionalized carboxylic acids with a chain length of from $\geq 6$ to $\leq 22$ carbon atoms, b5) N-acylamino acids, such as sarcosinates, glutamates, aspartates, preferably comprising an aliphatic or aromatic, linear or branched, optionally unsaturated and/or hydroxyfunctionalized radical with a chain length of $\geq 6$ to $\leq 22$ carbon atoms, or b6) carboxylates, sulfates, sulfonates, phosphonates or phosphates, preferably comprising an aliphatic or aromatic, linear or branched, optionally unsaturated and/or hydroxyfunctionalized acyl radical with a chain length of $\geq 6$ to $\leq 22$ carbon atoms, or mixtures thereof.

The emulsifiers of type b) are present in the emulsifier formulation preferably in at least partially neutralized form. It can be advantageous if they are already used as (partially) neutralized components. If desired, the neutralization step, however, can also take place in a suitable subsequent process step, in which case, for the purposes of the neutralization, preference is given to using bases which lead to anion-active emulsifiers with mono- or divalent cationic counterions. Particularly preferred counterions here are sodium and potassium.

Preference is given to using partially neutralized or neutralized citric acid partial esters as emulsifiers of type b), the hydrophobic radicals of which preferably in each case contain $\geq 10$ to $\leq 18$ carbon atoms.

Very particular preference is given to partial esters of citric acid and lauryl alcohol or of citric acid and glycerol mono- or dilaurates, and also partial esters of citric acid and oleyl alcohol or citric acid and glyceryl mono- or dioleates.

The emulsifier mixture A1) is preferably composed of $\geq 75$ to $\leq 99.5\%$ by weight of nonionic primary emulsifier component (a) and $\geq 0.5$ to $\leq 25\%$ by weight of acid-group-containing emulsifier component b), based on the emulsifier mixture A1).

Within the context of the present invention, cosurfactants B) are understood in particular as meaning those compounds which are characterized by interfacial activity, which can manifest itself in the reduction of interfacial tensions or the intercalation into interfacial films, without these substances, however, per se exhibiting the aggregation typical of surfactants to give micellar structures in water, or the stabilization of emulsion droplets typical of emulsions.

Within the context of the present invention, cosurfactants B) are moreover or alternatively understood to be in particular those compounds which have an HLB value according to Griffin between $\geq 4$ to $\leq 10$. Particularly preferably, these cosurfactants are characterized by an octanol-water partition coefficient log P or log $K_{ow}$ which is between 1 and 2. The octanol-water partition coefficient is calculated from the log 10 of the quotient of the amount of a substance dissolved at equilibrium at room temperature in octanol and in water (see: Ullmann's Encyclopedia of Industrial Chemistry, Volume B 7, (Volume Editor: E. Weise), 5th edition, VCH, Weinheim 1995, p. 78.

The cosurfactants B) present according to the invention are advantageously nonionic organic compounds with 4 to 14 carbon atoms which contain one or more polar groups in the molecule.

Preferred nonaromatic cosurfactants B) are, for example, aliphatic alcohols such as butanol, pentanol, hexanol, octanol, hexanediol or octanediol. According to one preferred embodiment of the invention, the cosurfactants used are n-pentanol, n-hexanol, 1,2-hexanediol, 1,2-heptanediol or 1,2-octanediol.

Furthermore, cosurfactants B) which can be used are preferably also monoalkyl ethers or monoalkyl esters based on glycerol, ethylene glycol, propylene glycol or diethylene glycol with fatty acids or alcohols having 6 to 10 carbon atoms.

According to one preferred embodiment of the invention, the cosurfactants B) used are aromatic cosurfactants. For the purposes of the present invention, aromatic cosurfactants are understood as meaning in particular interface-active substances which contain one or more aryl groups and which per se do not form any micellar structures in water.

It may be advantageous if these aromatic cosurfactants additionally also have antimicrobial properties, i.e. they are aromatic cosurfactants with preserving properties. The use of such cosurfactants permits the production of O/W emulsions according to the invention which ideally make do without further preservatives. Moreover, the addition of further customary preservatives (as auxiliaries and additives) is naturally possible, as are described, for example, in DE102005011785.6.

Aromatic cosurfactants B) with preserving properties that are particularly preferred according to the invention are phenoxyethanol and benzyl alcohol, alone or in combination with one or more alkyl paraben esters, preferably methyl paraben, ethyl paraben, propyl paraben, isopropyl paraben, butyl paraben and/or isobutyl paraben. Particular preference is given to the use of mixtures of alkyl paraben esters and phenoxyethanol, as are commercially available, for example, under the trade names Euxyl® K 300 (Schülke & Mayr) or Phenonip® (Clariant).

As mentioned, it is also possible to use mixtures of the specified preserving-active aromatic cosurfactants with other suitable preservatives. Thus, for example, it is also possible to use a mixture of phenoxyethanol and ethylhexylglycerol, as is commercially available under the name Euxyl PE 9010 (Schülke & Mayr).

It may also be advantageous if the O/W emulsion according to the invention has mixtures of the aforementioned cosurfactants, e.g. mixtures of aromatic and nonaromatic cosurfactants.

Preferred O/W emulsions according to the invention have at least one aliphatic cosurfactant B), selected from the group comprising n-pentanol, n-hexanol, 1,2-hexanediol, 1,2-heptanediol and 1,2-octanediol and/or at least one aromatic cosurfactant B), selected from the group comprising phenoxyethanol, benzyl alcohol and alkyl paraben esters alone or in mixtures with one another and/or in mixtures with customary preservatives.

For the purposes of the present invention, oils C) are understood in particular as meaning compounds selected from the group of Guerbet alcohols based on fatty alcohols having 6 to 20, preferably 8 to 10, carbon atoms, esters of linear $C_1$-$C_{44}$-fatty acids with linear $C_1$-$C_{22}$-fatty alcohols, esters of branched $C_1$-$C_{44}$-carboxylic acids with linear $C_1$-$C_{22}$-fatty alcohols, esters of linear $C_1$-$C_{44}$-fatty acids with branched alcohols, esters of linear and/or branched fatty acids with polyhydric alcohols and/or Guerbet alcohols, triglycerides based on $C_1$-$C_{44}$ fatty acids, vegetable oils, branched primary alcohols, substituted cyclohexanes, Guerbet carbonates, dialkyl(ene) ethers, dialkyl(ene) carbonates and/or aliphatic or naphthenic hydrocarbons, silicone oils, dimethicones, cyclomethicones, ethoxylated and/or propoxylated organic alcohols, ethoxylated and/or propoxylated organic acids or mixtures thereof. Within the context of the invention, perfume oils known to the person skilled in the art can also function as oil phases.

According to one preferred embodiment of the invention, the oils used are ester oils, oils based on ether, hydrocarbons, and also propoxylated organic alcohols and mixtures of these compounds.

As ester oils, in particular mono- or diesters of linear and/or branched mono- and/or dicarboxylic acids having $\geq 2$ to $\leq 44$ carbon atoms with linear and/or branched (in particular 2-ethylhexanol), saturated or unsaturated alcohols having $\geq 1$ to $\leq 22$ carbon atoms may be present in the O/W emulsions according to the invention as oils C). Likewise, the esterification products of aliphatic, difunctional or trifunctional alcohols (in particular dimerdiol and/or trimerdiol) having $\geq 2$ to $\leq 36$ carbon atoms with one or more monofunctional aliphatic carboxylic acids having $\geq 1$ to $\leq 22$ carbon atoms may be present. Also further suitable according to the invention are ester oils which contain aromatic groups.

The partial use of ester oils which have wax-like character at room temperature, such as, for example, myristyl myristate, can lead to a richer skin feel of the emulsions.

As ether oils, in particular dialkyl ethers having $\geq 4$ to $\leq 24$ carbon atoms can be present. Of preferred suitability according to the invention are saturated $C_6$-$C_{18}$-dialkyl ethers, such as, for example, di-n-octyl ether, di(2-ethylhexyl) ether, lauryl methyl ether or octyl butyl ether, and also didodecyl ether.

Preferred oil components are the cosmetic ester oils ethylhexyl palmitate, ethylhexyl stearate, decyl cocoate, diethylhexyl carbonate, dioctyl carbonate, cetearyl ethylhexanoate, decyl oleate, isocetyl palmitate, cetearyl isononanoate, hexyl laurate, isopropyl isononanoate, isopropyl palmitate, isopropyl myristate, isopropyl laurate and $C_{12-15}$ alkyl benzoate, stearyl heptanoate, and also the cosmetic ether oil dicaprylyl ether and the propoxylated organic alcohols PPG15-stearyl ether or PPG-4-butyl ether, and mixtures of the specified compounds.

Particularly preferred oils C) are cosmetic ester or ether oils selected from the group comprising ethylhexyl palmitate, ethylhexyl stearate, decyl cocoate, diethylhexyl carbonate, dioctyl carbonate, cetearyl ethylhexanoate, decyl oleate, isocetyl palmitate, cetearyl isononanoate, hexyl laurate, isopropyl isononanoate, isopropyl stearate, isopropyl palmitate, isopropyl myristate, isopropyl laurate, $C_{12-15}$-alkyl benzoate, dicaprylyl ether, mineral oil, isohexadecane, cyclopentasiloxane, octyldodecanol, stearyl heptanoate or mixtures of these compounds.

Within the context of the present invention, optionally present "polar solubilizers" are understood as meaning polar compounds which can be added in amounts of up to 10% by weight to the oil phases described below in one specific embodiment of the present invention in order to obtain clear oil phases. These are preferably water, glycols, polyalkylene glycols, glycerol, polyglycerol and short-chain alcohols such as ethanol or isopropanol. Preferably, glycerol or polyglycerol is present as solubilizer in the O/W emulsion according to the invention.

Auxiliaries and additives E) which may be used and/or present in the oil-in-water emulsion according to the invention are optionally all auxiliaries and additives known as prior art to the person skilled in the art in this field, such as e.g. oils and waxes, consistency regulators, thickeners e.g. based on polymer, inorganic and organic UV photoprotective filters, self-tanning agents, pigments, antioxidants, hydrotropes, deodorants and antiperspirant active ingredients, pH regulators, active ingredients, dyes, care substances, odor correctors, plant extracts, stabilizers, humectants, additional preservatives and perfumes or mixtures thereof, as are described, for example, in DE102005011785.6.

The auxiliaries and additives here can be added to the oil phase or to the water phase and/or to the dilution water in the production process of the emulsion.

As active ingredients, the O/W emulsions according to the invention preferably have those selected from tocopherol, tocopherol acetate, tocopherol palmitate, ascorbic acid, deoxyribonucleic acid, coenzyme Q10, retinol and retinyl derivatives, bisabolol, allantoin, phytantriol, panthenol, AHA acids, amino acids, hyaluronic acid, creatine (and creatine derivatives), guanidine (and guanidine derivatives), ceramides, phytosphingosine (and phytosphingosine derivatives), sphingosine (and sphingosine derivatives), pseudoceramides, essential oils, peptides, protein hydrolyzates, plant extracts and vitamin complexes.

The oil-in-water emulsions according to the invention preferably have a content of surfactants F) of from 0.025 to 5% by weight, preferably from 0.05 to 3% by weight and particularly preferably from 0.1 to 1.5% by weight. As a result of the low content of surfactants, the surprisingly good stability of the emulsions according to the invention and the good skin compatibility of the cream foams produced from these emulsions is achieved.

As surfactants (foam surfactants) F), the O/W emulsions according to the invention can preferably have one or more cationic, one or more anionic and/or one or more amphoteric and/or one or more nonionic surfactants.

Preferably, the O/W emulsions according to the invention have, as surfactants F), one or more surfactants selected from isethionates, sulfosuccinates, amphopropionates, betaines, amphoacetates, glycosides, amino acid surfactants, lauryl ethers, in particular polyethylene glycol lauryl ether, and sarcosinates, preferably selected from the sarcosinates.

The O/W emulsions according to the invention can have, as surfactant F), e.g. one or more surfactants from the group comprising sodium cocoyl isethionate (available under the trade name Hostapon® SCI-78C, Clariant), sodium lauroyl sarcosinate (available under the trade name Crodasinic® LS30, Croda Inc. or available under the trade name Perlastan L-30, Schill+Seilacher), disodium laureth sulfosuccinate (available under the trade name REWOPOL® SB FA 30 B, Evonik Goldschmidt GmbH), sodium cocoamphopropionate (available under the trade name REWOTERIC® AM KSF 40, Evonik Goldschmidt GmbH), fatty alcohol $C_{8-14}$-alkyl glycoside (available under the trade name Glucopon® 650 EC/HH, Cognis), disodium cocoyl glutamate (available under the trade name Plantapon® ACG 35, Cognis), such as, for example, TEGO® Betain 810 (Evonik Goldschmidt GmbH) or PEG-6 lauryl ether, such as e.g. Rewopal® LA 6 (Evonik Goldschmidt GmbH).

It may be advantageous if O/W emulsions which are based on PIT microemulsions have amphoteric surfactants as surfactant F). Preferably, O/W emulsions which are based on PIT microemulsions have exclusively amphoteric surfactants as surfactant F). Preferred amphoteric surfactants are betaines, such as e.g. the aforementioned TEGO® betaine 810.

As component H, the O/W emulsion according to the invention can comprise e.g. gingko, panthenol, creatine or allantoin.

In the O/W emulsion according to the invention, the mass ratio of surfactant F) to emulsifier mixture A) is preferably from 1:20 to 2:1, preferably 1:5. The ratio of oils C) to emulsifier mixture A) is preferably 20:1 to 1:2, preferably 10:1 to 1:1.

The emulsions according to the invention can be produced in various ways known to the person skilled in the art. In particular, the O/W emulsions according to the invention can be produced by phase inversion concentration methods (PIC methods) or by phase inversion temperature methods (PIT methods). These methods are adequately described in the prior art. The PIC method is described e.g. in DE 10 2005 011 785 and DE 10 2006 004353, and the literature cited therein. The PIT method is described e.g. in K. Shinoda, H. Kunieda, Phase Properties of Emulsions: PIT and HLB, Encycl. of Emulsion Technology, 337-367 (1), 1983 or Th. Förster, F. Schambil, W. von Rybinski, J. Disp. Sci. And Technology, 13(2), 183-93 (1992), and also in EP 1 268 740 and WO 00/04230.

It may be advantageous if the oil-in-water emulsion according to the invention has a concentration of inorganic salts of less than 0.1% by weight, based on the total composition. Preferred O/W emulsions according to the invention have no inorganic salts or from 10 wppm (ppm by mass) to 0.01% by weight of inorganic salts. Inorganic salts are to be understood as meaning in particular alkali metal and alkaline earth metal salts of mineral acids, such as e.g. hydrohalic acids, sulfuric acid, carbonic acid, phosphoric acid, or sulfurous acid.

Preferably, the oil-in-water emulsion according to the invention is obtained and/or produced by the method according to the invention described below.

The method according to the invention for producing a foamable oil-in-water emulsion is characterized in that an oil phase O) comprising
  A) one or more emulsifiers, where at least one nonionic emulsifier is present,
  B) one or more cosurfactants,
  C) one or more oils,
  D) ≥0 to <10% by weight, based on the total oil phase, of one or more polar solubilizers,
  E) optionally, in particular customary auxiliaries und additives,
is adjusted, by adding water G), which optionally comprises water-soluble substances H) which do not fall under components A to F, and one or more surfactants F) to a total water content of ≥70% by weight and a content of surfactant(s) F) of from 0.01 to less than 10% by weight. In preferred embodiments of the method according to the invention, the amount of water used and surfactant F) is selected such that the aforementioned foamable oil-in-water emulsions preferred according to the invention are obtained.

Emulsifiers or emulsifier mixtures which can be used are those which consist exclusively of nonionic emulsifiers, or emulsifier mixtures A1) consisting of: a) at least one nonionic primary emulsifier and b) at least one secondary emulsifier containing one or more acid functions and whose acid function can optionally be completely or partially neutralized. Preference is given to using emulsifier mixtures A1) which consist of the components a) and b).

The components A) to H) to be used or to be used preferably correspond to those specified previously. The amounts in which the components are used are preferably selected such that the concentrations given in the description of the O/W emulsions according to the invention are achieved.

The addition of the surfactant or of the surfactants F), preferably in an amount which leads to the aforementioned preferred concentrations, can take place together with the water and/or the aqueous phase, or subsequently. If the addition takes place together with the water, the surfactant can be mixed with the water and/or dissolved in it, or else be added separately but at the same time as the water. Preferably, the addition of the surfacants F) takes place separately following the addition of the water and/or of the aqueous phase. The addition of the surfactant takes place particularly preferably as the last component.

The O/W emulsions according to the invention can in principle be produced using a simple stirrer. Here, no additional homogenization step is required.

The production preferably takes place at room temperature by directly pouring in an oil phase comprising an emulsifier mixture A), cosurfactants B), oils C) and optionally solubilizer D) and customary auxiliaries and additives E) into the aqueous phase of water G) and optionally water-soluble substances H). Preferably, the method is carried out such that the oil phase used is clear and homogeneous.

If necessary, the oil phase can be converted into a clear phase by adding up to 10% by weight of a polar solubilizer D). Such polar solubilizers can be those mentioned above or water. Preference is given to using water as polar solubilizer. The use of solubilizers is particularly preferred when, in the production of the O/W emulsion according to the invention, firstly a concentrate is produced which is then diluted.

The use of homogeneous, clear oil phases is advantageous for producing finely divided O/W emulsions according to the invention since the use of cloudy oil phases often leads to coarser emulsions, the long-term stability of which is often inadequate. The transition from clear to cloudy oil phases here is fluid. The degree of clouding at which emulsions with adequate long-term stability can still be produced is dependent on the type and amount of components used and should be determined individually in these borderline cases.

As an alternative to the specified method, finely divided oil-in-water emulsions according to the invention can also take place via the intermediate step of a clear to transparent microemulsion-like concentrate. This concentrate consists generally of >30 to ≤90% by weight of oil phase, preferably of ≥40-≤80% by weight of oil phase, comprising an emulsifier mixture A), cosurfactants B), oils C) and optionally polar solubilizers D) and/or customary auxiliaries and additives E), and also a water phase. These clear to transparent microemulsion-like concentrates are preferably produced at room temperature by stirring water into the oil phase. For producing these concentrates, it is also possible to use cloudy oil phases. Here, the optimum water content of the concentrates is dependent on the formulation (e.g. on the oil used), but is generally ≥10 to <70% by weight, preferably ≥20 to ≤60% by weight.

Finally, these microemulsion-like concentrates can be diluted to give oil-in-water emulsions according to the invention. In this connection, both the production of the microemulsion-like concentrates, and also the final dilution step at room temperature can take place using a simple stirrer. The dilution preferably takes place at a temperature of less than 40° C.

The oil phases can be produced by the known methods of the prior art. For example, depending on the consistency and concentration of the components used, the oil phases can be produced at temperatures in the range from ≥20 to ≤75° C. by simply mixing the components. These oil phases can be used at room temperature for producing the oil-in-water emulsions according to the invention.

The O/W emulsion according to the invention can be used e.g. for producing foam and/or cream foam according to the invention. The foam or cream foam according to the invention is characterized in that it is obtainable by foaming an oil-in-water emulsion according to the invention. Foam or cream foam preferably contain air in the foam bubbles as gas mixture. Particularly preferably, foam or cream foam contain no synthetic gas mixture, in particular no synthetic, in particular organic propellant gases.

The volume ratio of gas mixture to O/W emulsion in the foam or cream foam is preferably from 3:1 to 50:1, preferably from 6:1 to 30:1.

The foam or cream foam according to the invention can be obtained by foaming the O/W emulsion according to the invention. The foaming takes place preferably by introducing a gas mixture, preferably air, preferably ambient air. The introduction of the gas mixture preferably takes place without pressure. Preferably, foams which are produced using synthetic gas mixtures do not form part of the present invention. Within the context of the present invention, ambient air is understood as meaning air which is available in the vicinity of the foaming apparatus as ambient atmosphere. Ambient air is thus not understood as meaning compressed air provided in a relatively large storage container.

The foaming can take place in a standard commercial foaming apparatus. Such foaming apparatuses are commercially available e.g. as pump foam systems from the companies Airspray (the Netherlands), Keltec (the Netherlands), Ophardt (Germany), Brightwell (UK), Taplast (Italy) and Supermatic (Switzerland). Suitable foaming apparatuses are e.g. Taplast foamer Pump PIUMA 262/400, Taplast foamer pump PIUMA 263/400, Rexam Airspray: F2—Elegant Finger Pump Foamer, Rexam Airspray: F3—Elegant Finger Pump Foamer, Rexam Airspray: G3—Elegant Finger Pump Foamer, Rexam Airspray: M3—Mini Foamer, Rexam Airspray: T1—Table Top Foamer and from Rieke Packaging Systems the models RF—08 Finger Tip Foamer and RF—17 Palm Foamer.

The special feature of the method according to the invention is that the oil-in-water emulsion according to the invention can be foamed without homogenization (shaking) carried out directly prior to the foaming. Consequently, the oil-in-water emulsion according to the invention can also be used in fixedly installed foam dispensers, for which shaking of the emulsion prior to use is impossible.

The oil-in-water emulsions according to the invention can be used e.g. for producing cosmetic, dermatological or pharmaceutical foams or household cleaner foams, in particular for producing such cream foams. These foams or cream foams can be used e.g. for face and body care, baby care, as skin protection of sunscreen preparation and/or as make-up remover. The foam according to the invention can be e.g. a cleaning and care preparations for skin and skin appendages. The foams according to the invention can also be used for the cleaning and care of surfaces in the home and in industry, such as, for example, textile care, leather care, the care and cleaning of metallic or nonmetallic surfaces, for example for the cleaning and care of automobiles or furniture.

The examples below describe, by way of example, the subject matter of the present invention without any intention of limiting the invention to these embodiments.

Unless noted otherwise, all % data are data in % by weight. The concentration data in all of the examples are given as % by weight, unless noted otherwise. The weight data refer here to the presentation form and not to the active substance.

EXAMPLES

The following substances were used in the examples below:

Gingko extract: Vegetol® Gingko *Biloba* LC416 Hydro=aqueous gingko extract (Gattefosse)

Perlastan L 30: sodium laurylsarcosinate (Schill & Seilacher)

Meadowfoam seed oil: extracted oil from the seeds from *Limnanthes Alba*

Hostapon SCI: sodium coconut fatty acid isethionate (Clariant)

Glucopon 650: C8-C16 polyalkyl glucoside (Cognis)

Plantapon ACG: sodium cocoyl glutamate (Cognis)

Laureth 6.: Rewopal LA6 (Evonik Goldschmidt)

Emulgade CM: Cetearyl Isononate and Ceteareth-20 and Cetearyl Alcohol and Glyceryl Stearate and Glycerol and Ceteareth-12 and Cetyl Palmitate (Cognis)

Eumulgin HRE 40: PEG-40 hydrogenated castor oil (Cognis)

Tego® Wipe DE: mixture of diethylhexyl carbonate, polyglyceryl-4 laurate; phenoxyethanol; methylparaben, dilauryl citrate; ethylparaben; butylparaben; propylparaben and isobutylparaben; (Evonik Goldschmidt)

Tego® Wipe Flex: mixture of 56% emollient (ethylhexyl stearate) 29% emulsifier (sorbitan laurate; polyglyceryl-4 laurate; dilauryl citrate), 15% phenoxyethanol (ethylhexyl stearate, phenoxyethanol, polyglyceryl-4 laurate, sorbitan laurate and dilauryl citrate); (Evonik Goldschmidt)

Tego® Wipe R4: 66% emollients (ethylhexyl stearate; cotton seed oil), 22% emulsifiers (sorbitan laurate; polyglyceryl-4 laurate; dilauryl citrate), 12% phenoxyethanol (Evonik Goldschmidt)

Rewopol® SB FA 30 B: disodium laureth sulfosuccinate (Evonik Goldschmidt)

Rewoteric® AM KSF 40: sodium cocoamphopropionate (Evonik Goldschmidt)

TEGINACID® H: mixture of glyceryl stearate and ceteth-20 (Evonik Goldschmidt)

Tegosoft® CR: cetyl ricinoleate (Evonik Goldschmidt)

Tegosoft® Liquid: cetearyl ethylhexanoate (Evonik Goldschmidt)

Tegosoft® APS: PPG-11 stearyl ether (Evonik Goldschmidt)

Tegosoft® SH: stearyl heptanoate (Evonik Goldschmidt)

Tegosoft® P: isopropyl palmitate (Evonik Goldschmidt)

Tegosoft® DC: decyl cocoate (Evonik Goldschmidt)

Tegosoft® TN: C12-15 alkyl benzoate (Evonik Goldschmidt)

Tegosoft® DEC: diethylhexyl carbonate (Evonik Goldschmidt)

TEGO® Alkonaol 18: stearyl alcohol (Evonik Goldschmidt)
TEGO® Betain 810: capryl/capramidopropyl betaine (Evonik Goldschmidt)
TEGO® Cosmo C 100: creatine (Evonik Goldschmidt)
VARISOFT® PATC: palmitamidopropyltrimonium chloride (Evonik Goldschmidt)
Crodasinic LS30/NP: sodium lauroyl sarcosinate (Croda)

Example 1

Production of O/W Emulsions According to the Invention starting from PIC microemulsions Formulations were produced from the components given in Tables 1 to 3. For this purpose, firstly a microemulsion was produced from the components referred to by M.

The microemulsion was then obtained by mixing all of the components listed under M, with the exception of the water, with stirring to give a clear and homogeneous oil phase. This oil phase was then poured into water at room temperature, the water or the aqueous phase being stirred using a single manual stirrer.

The components of the microemulsion given under S were then added with stirring.

TABLE 1

Example formulations produced via PIC microemulsions
(data in % by mass based on the end formulation)

|   | Components | 1a | 1b | 1c | 1d | 1e | 1f | 1g |
|---|---|---|---|---|---|---|---|---|
| M | Water | 85.0 | 90.0 | 93.0 | 91.5 | 85.0 | 91.0 | 90.0 |
|   | Tego Wipe DE | 11.4 | 5.7 |  |  | 11.4 | 5.0 |  |
|   | Tego Wipe R4 |  |  | 5.0 | 5.0 |  |  | 5.0 |
| S | Crodasinic LS30/NP | 3.6 | 4.3 | 2.0 | 3.5 |  | 3.0 | 4.9 |
|   | Perlastan L-30 |  |  |  |  | 3.6 |  |  |
|   | Phenoxyethanol |  |  |  |  |  | 1.0 |  |
|   | Perfume |  |  |  |  |  |  | 0.1 |
|   | Foamability | yes | yes | yes | yes | yes | yes | yes |
|   | Foam stability (%) | 75% | 75% | 75% | 75% | 75% | 75% | 75% |
|   | Foamability after storage for 3 months at 40° C. | yes | yes | yes | yes | yes | yes | yes |
|   | Stability in the 3 temperature ranges | stable | stable | stable | stable | stable | stable | stable |

TABLE 2

Example formulations produced via PIC microemulsions
(data in % by mass, based on the end formulation)

|   | Components | 1h | 1i | 1j | 1k | 1l | 1m | 1n |
|---|---|---|---|---|---|---|---|---|
| M | Water | 90.3 | 90.3 | 90.3 | 90.3 | 91.5 | 91.5 | 92.9 |
|   | Tego Wipe Flex | 4.0 | 4.0 | 4.0 | 4.0 | 4.0 | 4.0 | 4.0 |
|   | Tegosoft CR | 0.8 |  |  |  |  |  |  |
|   | Meadowfoam seed Oil |  | 0.8 |  |  |  |  |  |
|   | Tegosoft liquid |  |  | 0.8 |  |  |  |  |
|   | Tegosoft APS |  |  |  | 0.8 |  |  |  |
|   | Tegosoft SH |  |  |  |  | 0.8 | 0.8 | 0.8 |
| S | Crodasinic LS30/NP | 4.9 | 4.9 | 4.9 | 4.9 |  |  |  |
|   | Rewoteric AM KSF |  |  |  |  | 3.7 |  |  |
|   | Rewopol SB FA 30 |  |  |  |  |  | 3.7 |  |
|   | Hostapon SCI |  |  |  |  |  |  | 2.3 |
|   | Foamability | yes | yes | yes | yes | yes | yes | yes |
|   | Foam stability (%) | 100 | 75 | 100 | 75 | 75 | 100 | 75 |
|   | Foamability after storage for 3 months at 40° C. | yes | yes | yes | yes | yes | yes | yes |
|   | Stability in the 3 temperature ranges | stable | stable | stable | stable | stable | stable | stable |

TABLE 3

Example formulations produced via PIC microemulsions
(data in % by mass, based on the end formulation)

|   | Component | 1o | 1p | 1q | 1r | 1s | 1t | 1u |
|---|---|---|---|---|---|---|---|---|
| M | Water | 93.3 | 92.1 | 94.0 | 90.1 | 94.0 | 94.0 | 94.0 |
|   | Tego Wipe Flex | 4.0 | 4.0 | 4.0 | 4.0 | 4.0 | 4.0 | 4.0 |
|   | Tegosoft SH | 0.8 | 0.8 | 0.8 | 0.4 | 0.4 | 0.4 | 0.4 |
|   | Gingko extract |  |  |  | 0.1 | 0.1 | 0.1 | 0.1 |
|   | Phenoxyethanol |  |  |  | 0.4 | 0.4 | 0.4 | 0.4 |
|   | Silk Beauty |  |  |  | 0.1 | 0.1 | 0.1 | 0.1 |
| S | Glucopon 650 | 1.7 |  |  |  |  |  |  |
|   | Crodasinic LS30/NP |  |  |  | 4.9 | 1.0 |  |  |
|   | Plantapon ACG |  | 2.9 |  |  |  |  |  |
|   | Laureth-6 |  |  | 0.3 |  |  |  |  |
|   | Rewopol SB FA 30 |  |  |  |  |  | 1.0 | 0.3 |
|   | Perfume | 0.2 | 0.2 | 0.2 |  |  |  |  |
|   | Foamability | yes | yes | yes | yes | yes | yes | yes |
|   | Foam stability (%) | 75 | 100 | 50 | 100 | 100 | 100 | 100 |
|   | Foamability after storage for 3 months at 40° C. | yes | yes | yes | yes | yes | yes | yes |
|   | Stability in the 3 temperature ranges | stable | stable | stable | stable | stable | stable | stable |

Example 2

Production of O/W Emulsions According to the Invention Starting from PIT Microemulsions Formulations were produced from the components given in Table 4. For this purpose, firstly a microemulsion was produced from the components listed under M by stirring the specified components.

The components of the microemulsion given under S were then added with stirring.

TABLE 4

Example formulations produced via PIT microemulsions
(data in % by mass, based on the end formulation)

| | Components | 2a | 2b | 2c | 2d | 2e | 2f |
|---|---|---|---|---|---|---|---|
| M | Water | 73.65 | 77.55 | 74.85 | 74.85 | 75.65 | 74.85 |
| | Emulgade CM | 15.00 | 15.00 | 15.00 | 15.00 | 15.00 | 15.00 |
| | Glycerol 99.5% vegetable | 5.00 | 5.00 | 5.00 | 5.00 | 5.00 | 5.00 |
| | Eumulgin HRE 40 | 0.35 | 0.35 | 0.35 | 0.35 | 0.35 | 0.35 |
| | Vitamin E acetate | 0.10 | 0.10 | 0.10 | 0.10 | 0.10 | 0.10 |
| | Preservative | 0.85 | 0.85 | 0.85 | 0.85 | 0.85 | 0.85 |
| | Perfume oil | 0.15 | 0.15 | 0.15 | 0.15 | 0.15 | 0.15 |
| S | Crodasinic LS30/NP | 4.90 | 1.00 | | | | |
| | Rewoteric AM KSF | | | 3.70 | | | |
| | Rewopol SB FA 30 | | | | 3.70 | | |
| | Glucopon 650 | | | | | 2.90 | |
| | Plantapon ACG | | | | | | 3.70 |
| | Foamability | yes | yes | yes | yes | yes | yes |
| | Foam stability (%) | 100 | 75 | 75 | 100 | 75 | 75 |
| | Foamability after storage for 3 months at 40° C. | yes | yes | yes | yes | yes | yes |
| | Stability in the 3 temperature ranges | stable | stable | stable | stable | stable | stable |

Example 3

Producing O/W Emulsions not According to the Invention in Accordance with the Prior Art O/W emulsions were produced from the components given in Tables 5 to 11. The production was carried out as stated in the corresponding documents.

TABLE 5

Composition of the O/W emulsion in accordance with Uniquema, as described in the formula (WI 2025-109/1) from the formula collection from Uniquema (data in % by mass)

| | |
|---|---|
| Arlasolve 200 Liquid/GEL | 3.800 |
| Arlacel 987 | 1.100 |
| Atlas G-2330 | 3.000 |
| Arlamol E | 3.500 |
| Prisorine 2021 | 8.000 |
| Prisorine 2034 | 1.000 |
| Bronopol 30% strength | 0.270 |
| Pricerine 9091 (glycerol) | 4.000 |
| Town water | 41.730 |
| Arlasilk Phospholipid PLN | 2.000 |
| Propylene glycol (1,2-propanediol) | 3.000 |
| Town water 2 | 20.000 |
| Tego Betain 810 | 8.600 |
| Foamability | yes |
| Foam stability (%) | 50 |
| Foamability after storage for 3 months at 40° C. | no |
| Stability in the 3 temperature ranges | unstable at 40° C. |

TABLE 6

Composition of the O/W emulsion in accordance with formula WR 19/01-19 of the formula collection from Evonik Goldschmidt GmbH, which can be seen on their Internet site (data in % by mass).

| | | |
|---|---|---|
| Teginacid H | Phase A | 3.900 |
| Tego Alkanol 18 | | 1.300 |
| Tegosoft P | | 3.900 |
| Tegosoft DC | | 3.200 |
| Tegosoft TN | | 2.500 |

TABLE 6-continued

Composition of the O/W emulsion in accordance with formula WR 19/01-19 of the formula collection from Evonik Goldschmidt GmbH, which can be seen on their Internet site (data in % by mass).

| | | |
|---|---|---|
| Glycerin Ph EurIII 99.5% | Phase B | 1.500 |
| Water | | 77.000 |
| Tego Betain 810 | Phase C | 6.000 |
| Phenonip | Phase D | 0.700 |
| Foamability | | yes |
| Foam stability (%) | | 50 |
| Foamability after storage for 3 months at 40° C. | | no |
| Stability in the 3 temperature ranges | | unstable at 40° C. |

TABLE 7

Composition of the O/W emulsion in accordance with formula ADP-5545-160 as described in the formula collection from Evonik Goldschmidt GmbH (data in % by mass).

| | | |
|---|---|---|
| Varisoft PATC | Phase A | 6.000 |
| Tego Alkanol 18 | | 2.000 |
| Tegosoft P | | 6.000 |
| Tegosoft DC | | 3.000 |
| Tegosoft TN | | 3.000 |
| Amilan Guar 36 | | 0.750 |
| Glycerin | Phase B | 3.000 |
| Water | | 67.050 |
| Tego Cosmo C100 | | 0.500 |
| Tego Betain 810 | Phase C | 8.000 |
| Phenonip | Phase D | 0.700 |
| Citric acid 10% strength | Phase E | 1.253 |
| Foamability | | yes |

TABLE 7-continued

Composition of the O/W emulsion in accordance with formula ADP-5545-160 as described in the formula collection from Evonik Goldschmidt GmbH (data in % by mass).

| | |
|---|---|
| Foam stability (%) | 50 |
| Foamability after storage for 3 months at 40° C. | no |
| Stability in the 3 temperature ranges | unstable at 40° C. |

TABLE 8

Composition of the O/W emulsion in accordance with formula ADP-5545-118 (Foaming Lotion with Varisoft PATC) as described in the formula collection from Evonik Goldschmidt GmbH (data in % by mass).

| | | |
|---|---|---|
| Varisoft PATC | Phase A | 6.000 |
| Tego Alkanol 18 | | 2.000 |
| Tegosoft P | | 6.000 |
| Tegosoft DC | | 3.000 |
| Tegosoft TN | | 3.000 |
| Glycerin Ph EurIII 99.5% | Phase B | 2.000 |
| Water | | 62.300 |
| Tego Betain 810 | Phase C | 15.000 |
| Phenonip | Phase D | 0.700 |
| Foamability | | yes |
| Foam stability (%) | | 50 |
| Foamability after storage for 3 months at 40° C. | | no |
| Stability in the 3 temperature ranges | | unstable at 40° C. |

TABLE 9

Composition of the O/W emulsions A, B and C in accordance with Emulsion pump foams Table 2/3 (Specialty Chemicals Magazine November 2005 page 38) (data in % by mass).

| Product name | Composition | | A | B | C |
|---|---|---|---|---|---|
| Imwitor 380 | Glyceryl cocoate/citrate/lactate | Phase A | 3.000 | 3.000 | 3.000 |
| Cosmacol EMI | di-C12-13-alkyl malate | Phase A | 3.000 | 3.000 | 3.000 |
| Cosmacol EOI | C12-13 alkyl octanoate | Phase A | 2.500 | 2.500 | 2.500 |
| Miglyol 812N | Caprylic/capric triglyceride | Phase A | 5.000 | 5.000 | 5.000 |
| Avocado Oil | Persea Gratissima oil | Phase A | 3.000 | 3.000 | 3.000 |
| Abil B 8839 | Cyclomethicone | Phase A | 1.500 | 1.500 | 1.500 |
| Glycerin Ph EurIII 99.5% | Glycerol | Phase B | 6.000 | 6.000 | 6.000 |
| Rhodicare S | Xanthan gum | Phase B | 0.500 | 0.500 | 0.500 |
| Water | | Phase B | ad 100 | ad 100 | ad 100 |
| Fragrance | | Phase C | q.s. | q.s. | q.s. |
| Tocopheryl acetate | Tocopheryl acetate | Phase C | 1.000 | 1.000 | 1.000 |
| Total | | | 100.000 | 100.000 | 100.000 |
| Fraction of the aforementioned formula A/B/C | | | 82.000 | 95.000 | 99.000 |
| Crodasinic LS 30 | | | 18.000 | 5.000 | 1.000 |
| Foamability | | | yes | no | no |
| Foam stability | | | 25% | 0% | 0% |
| Foamability after storage for 3 months at 40° C. | | | no | no | no |
| Stability in the 3 temperature ranges | | | unstable at 40° C. | unstable at 40° C. | unstable at 40° C. |

TABLE 10

Composition of the O/W emulsions A, B and C in accordance with Emulsion pump foams Table 2/3 (Specialty Chemicals Magazine November 2005 page 38) (in % by mass).

| Product name | Composition | | A | B | C |
|---|---|---|---|---|---|
| Ceralution C | Water + capric/caprylic triglyceride + glycerol + ceteareth-25 + Na-dicocoylethylenediamine PEG 15 sulfate + Na lauryl lactylate + behenyl alcohol + | Phase A | 10.000 | 10.000 | 10.000 |

TABLE 10-continued

Composition of the O/W emulsions A, B and C in accordance with Emulsion pump foams Table 2/3 (Specialty Chemicals Magazine November 2005 page 38) (in % by mass).

| Product name | Composition | | A | B | C |
|---|---|---|---|---|---|
| | glyceryl stearate + glyceryl stearate citrate + gum Arabic + xanthan gum + phenoxyethanol + methylparaben + ethylparaben + butylparaben + isobutylparaben | | | | |
| Miglyol 829 | Caprylic/capric/succinic triglyceride | Phase B | 7.000 | 7.000 | 7.000 |
| Cosacol EMI | di-C12-13-alkyl malate | Phase B | 2.000 | 2.000 | 2.000 |
| Avocado oil | Persea Gratissima oil | Phase B | 5.000 | 5.000 | 5.000 |
| Tocopheryl acetate | Tocopheryl acetate | Phase B | 1.000 | 1.000 | 1.000 |
| Water | Aqua | Phase C | 47.700 | 47.700 | 47.700 |
| Avicel in water | Aqua with 4% microcrystalline cellulose and cellulose gum | Phase C | 25.000 | 25.000 | 25.000 |
| Rhodicare S | Xanthan gum | Phase C | 0.300 | 0.300 | 0.300 |
| D-Panthenol 100% | Dexpanthenol | Phase C | 1.500 | 1.500 | 1.500 |
| Fragrance | Perfume | Phase D | q.s. | q.s. | q.s. |
| Preservative | Phenonip | Phase D | 1.000 | 1.000 | 1.000 |
| Total | | | 100.000 | 100.000 | 100.000 |
| Fraction of the aforementioned formulas A/B/C | | | 50.000 | 50.000 | 50.000 |
| Crodasinic LS 30 | | | 16.500 | 5.000 | 1.000 |
| Water | | | 33.500 | 45.000 | 49.000 |
| Foamability | | | yes | no | no |
| Foam stability | | | 25% | 0% | 0% |
| Foamability after storage for 3 months at 40° C. | | | no | no | no |
| Stability in the 3 temperature ranges | | | unstable at 40° C. | unstable at 40° C. | unstable at 40° C. |

TABLE 11

Composition of the O/W emulsion in accordance with formula OW 8-92/0 from the formula collection of Sasol AG (data in % by mass).

| Product name | Composition | | A |
|---|---|---|---|
| Water, deionized | Water | Phase A | 5.000 |
| Ceralution F | Sodium dicocoylethylenediamine PEG 15 sulfate and sodium lauryl lactylate | Phase A | 2.000 |
| Laracare A 200 | Galactoarabinan | Phase A | 0.500 |
| Glycerin Ph EurIII 99.5% | Glycerol | Phase A | 6.000 |
| Ceralution H | Behenyl alcohol and glyceryl stearate and glyceryl stearate citrate and sodium dicocoylethylenediamine PEG 15 sulfate | Phase B | 1.000 |
| Marlipal O13/120 | Caprylic/capric/succinic triglyceride | Phase B | 1.000 |
| Miglyol 812N | Caprylic/capric triglyceride | Phase B | 7.000 |
| Cosmacol EMI | di-C12-13-alkyl malate | Phase B | 3.000 |
| Avocado oil | Persea Gratissima oil | Phase B | 10.000 |
| Vitamin E acetate | Tocopheryl acetate | Phase B | 1.000 |
| Water | Water | Phase C | 61.500 |
| D-Panthenol 100% | Dexpanthenol | Phase C | 1.500 |
| Preservative | Phenonip | Phase D | 0.500 |
| Total | | | 100.000 |
| Fraction of the aforementioned formula A | | | 50.000 |
| Crodasinic LS 30 | | | 5.000 |
| Water | | | 45.000 |
| Foamability | | | yes |
| Foam stability | | | 25% |
| Foamability after storage for 3 months at 40° C. | | | no |
| Stability in the 3 temperature ranges | | | unstable at 40° C. |

Definition: Long-Term Stability

The O/W emulsions produced in examples 1 to 3 were stored in closed screw-top jars in a heating cabinet at RT, 40° C. and 4° C. in each case for 3 months (corresponding to IFSCC Monograph Number 2, page 8, chapter IV I a.) Following storage, a visual check was made whether a demixing/phase separation was observed, which points to destruction of the O/W emulsion (unstable). It was established that the O/W emulsions according to the invention as per examples 1 and 2 were still stable, whereas in the case of the comparison emulsions from example 3, in each case a demixing could be observed.

Definition: Testing the Foamability/Foam Stability

Experiments relating to the foamability of the examples and the stability of the foam were tested. For this purpose, the example formulas were transferred to an Elegant Foamer Line M3 foam dispenser from Rexam Airspray. Then, 10 pump strokes à 0.4 g of product were placed in a 5 cm high beaker with a capacity of 25 ml.

The initial foam height and the foam stability after 3 min was then evaluated. The product is foamable if the beaker can be filled by 10 pump strokes of the foam dispenser. Adequate foam stability is present if the foam height collapses after 3 minutes not by 50% or more than 50%. This can be shown clearly. The figure 75% gives an estimation which makes it clear that the foam has broken, but not by 50% or more. 100% indicates that the foam has not changed after 3 minutes. Foams with a figure of 100% or 75% have an adequate foam stability. Foams with a figure of 50% or less do not have an adequate foam stability, with foams having a figure of 25% and 0% being absolutely unacceptable as foam.

The results of the tests into long-term stability, foamability and foam stability are given in tables 1 to 11.

It is clearly evident that a good foamability of the O/W emulsions according to the invention is present and that the foams produced from the O/W emulsions according to the invention lead to a foam which is more stable than those foams which have been produced from O/W emulsions according to the prior art.

Absorption Behavior—Sensory Test

Test Procedure

The hands are cleaned with 1 g of Estesol® (skin cleaner from Evonik Stockhausen GmbH). After a drying time of 5 min, 0.75 g of reference product, here STOKO® soft+care (a gel from Evonik Stockhausen GmbH) or Stokolan® (an O/W cream from Evonik Stockhausen GmbH), is rubbed in and the absorption time is noted. The hands are then cleaned again with 1 g of Estesol® and, after 5 min, the test product according to the invention, here foam 1s, is applied. The absorption time is noted. A questionnaire is then completed.

Result of a Test Panel with 10 Subjects

The foam 1S absorbed 27% more quickly than STOKO® soft+care and 56% more quickly than Stokolan®.

In the direct comparison, 5 subjects preferred the foam 1s, 4 subjects STOKO® soft+care and 1 subject found both equally good.

In the direct comparison, 8 subjects preferred the foam 1s and 2 subjects Stokolan®.

The invention claimed is:

1. A cosmetic composition, comprising:
   a stable foam obtained from a foamable oil-in-water emulsion, said emulsion comprising:
   A) one or more emulsifiers, wherein at least one nonionic emulsifier is present,
   B) one or more co-surfactants,
   C) one or more oils,
   D) optionally one or more polar solubilizers,
   E) optionally one or more auxiliaries and/or additives,
   F) one or more surfactants selected from the group consisting of isethionates, sulfosuccinates, amphopropionates, betaines, amphoacetates, glycosides, amino acid surfactants, polyethylene glycol lauryl ether and sarcosinates,
   G) water, and
   H) optionally one or more water-soluble substances,
   with the proviso that the water content of the emulsion is ≥70% by weight and the content of surfactant (F) is from 0.01 to less than 10% by weight, based on the weight of the total emulsion;
   with the proviso that the composition does not contain a propellant gas;
   wherein the emulsifier A) is an emulsifier mixture A1) consisting of:
   a) at least one nonionic primary emulsifier, and
   b) at least one secondary emulsifier containing one or more acid functions and whose acid function is optionally completely or partially neutralized;
   wherein the primary nonionic emulsifier component (a) comprises one or more polyglycerol laurates or mixtures of polyglycerol laurates with one or more sorbitan laurates.

2. The cosmetic composition as claimed in claim 1, wherein said oil-in-water emulsion comprises, as surfactant (F), one or more surfactants selected from the group consisting of sodium cocoyl isethionate, sodium lauroyl sarcosinate, disodium laureth sulfosuccinate, sodium cocoamphopropionate, fatty alcohol C8-14-alkyl glycosides, disodium cocoyl glutamate, betaine and PEG-6 lauryl ether.

3. The cosmetic composition as claimed in claim 1, wherein in said oil-in-water emulsion, at least one auxiliary and/or additive (E) is present and is selected from the group consisting of pH regulators, consistency regulators, stabilizers, humectants, dyes, care substances, active ingredients, odor correctors, plant extracts, perfumes, preservatives, film formers and mixtures thereof.

4. The cosmetic composition as claimed in claim 1, wherein said oil-in-water emulsion comprises
   at least one aliphatic co-surfactant (B), selected from the group consisting of n-pentanol, n-hexanol, 1,2-hexanediol, 1,2-heptanediol and 1,2-octanediol,
   or
   at least one aromatic co-surfactant (B), selected from the group consisting of phenoxyethanol, benzyl alcohol and alkyl paraben esters,
   alone or in mixtures with one another and/or in mixtures with a preservative.

5. The cosmetic composition as claimed in claim 1, comprising, as secondary emulsifier component b), one or more partially neutralized or neutralized citric acid partial esters, the hydrophobic radicals of which contain in each case ≥10 to ≤18 carbon atoms.

6. The cosmetic composition as claimed in claim 1, wherein the emulsifier A) consists exclusively of nonionic emulsifiers.

7. A method for producing a foamable oil-in-water emulsion, comprising:
   mixing an oil phase comprising
   A) one or more emulsifiers, wherein at least one nonionic emulsifier is present,
   B) one or more cosurfactants,
   C) one or more oils,
   D) ≥0 to <10% by weight, based on the weight of the total oil phase, of one or more polar solubilizers,
   E) optionally auxiliaries and additives,
   is mixed with water G), which optionally comprises one or more water-soluble substances H), and one or more surfactants F) selected from the group consisting of isethionates, sulfosuccinates, amphopropionates, betaines, amphoacetates, glycosides, amino acid surfactants, polyethylene glycol lauryl ether and sarcosinates to give an emulsion with a water content of ≥70% by weight and a content of surfactants of from 0.01 to less than 10% by weight;

wherein the emulsifier A) is an emulsifier mixture A1) consisting of:
a) at least one nonionic primary emulsifier, and
b) at least one secondary emulsifier containing one or more acid functions and whose acid function is optionally completely or partially neutralized;
wherein the primary nonionic emulsifier component (a) comprises one or more polyglycerol laurates or mixtures of polyglycerol laurates with one or more sorbitan laurates, wherein the emulsion is able to form a stable foam.

8. The cosmetic composition as claimed in claim 1, wherein the foam bubbles contain air as gas mixture.

9. A method of producing a foam, comprising:
foaming an oil-in-water emulsion to obtain a stable foam, said oil-in-water emulsion comprising:
A) one or more emulsifiers, wherein at least one nonionic emulsifier is present,
B) one or more co-surfactants,
C) one or more oils,
D) optionally one or more polar solubilizers,
E) optionally one or more auxiliaries and/or additives,
F) one or more surfactants selected from the group consisting of isethionates, sulfosuccinates, amphopropionates, betaines, amphoacetates, glycosides, amino acid surfactants, polyethylene glycol lauryl ether and sarcosinates,
G) water, and
H) optionally one or more water-soluble substances,
with the proviso that the water content of the emulsion is ≥70% by weight and the content of surfactant (F) is from 0.01 to less than 10% by weight, based on the weight of the total emulsion;
with the proviso that the oil-in water emulsion does not contain a propellant gas;
wherein the emulsifier A) is an emulsifier mixture A1) consisting of:
a) at least one nonionic primary emulsifier, and
b) at least one secondary emulsifier containing one or more acid functions and whose acid function is optionally completely or partially neutralized;
wherein the primary nonionic emulsifier component (a) comprises one or more polyglycerol laurates or mixtures of polyglycerol laurates with one or more sorbitan laurates.

10. The method as claimed in claim 9, wherein said foam is a cosmetic, dermatological or pharmaceutical foam or a household cleaner foam.

11. The method as claimed in claim 9, wherein said foam is suitable for face and body care, baby care, as sunscreen and/or as make-up remover or for the cleaning and care of surfaces in the home and in industry.

12. The method as claimed in claim 9, wherein the foam is foamed by introducing ambient air.

13. A cosmetic composition, comprising:
a stable foam obtained from a foamable oil-in-water emulsion, said emulsion comprising:
A) one or more emulsifiers, wherein at least one nonionic emulsifier is present,
B) one or more co-surfactants,
C) one or more oils,
D) optionally one or more polar solubilizers,
E) optionally one or more auxiliaries and/or additives,
F) one or more foam surfactants selected from the group consisting of isethionates, sulfosuccinates, amphopropionates, betaines, amphoacetates, glycosides, amino acid surfactants, polyethylene glycol lauryl ether and sarcosinates which aid the production of foam without the use of a synthetic propellant,
G) water, and
H) optionally one or more water-soluble substances,
with the proviso that the water content of the emulsion is ≥70% by weight and the content of surfactant (F) is from 0.01 to less than 10% by weight, based on the weight of the total emulsion;
with the proviso that the composition does not contain a propellant gas; and
wherein the foam contains ambient air and does not contain a synthetic gas mixture;
wherein the emulsifier A) is an emulsifier mixture A1) consisting of:
a) at least one nonionic primary emulsifier, and
b) at least one secondary emulsifier containing one or more acid functions and whose acid function is optionally completely or partially neutralized;
wherein the primary nonionic emulsifier component (a) comprises one or more polyglycerol laurates or mixtures of polyglycerol laurates with one or more sorbitan laurates.

14. A method of producing a foam, comprising:
foaming an oil-in-water emulsion to obtain a stable foam, said oil-in-water emulsion comprising:
A) one or more emulsifiers, wherein at least one nonionic emulsifier is present,
B) one or more co-surfactants,
C) one or more oils,
D) optionally one or more polar solubilizers,
E) optionally one or more auxiliaries and/or additives,
F) one or more foam surfactants selected from the group consisting of isethionates, sulfosuccinates, amphopropionates, betaines, amphoacetates, glycosides, amino acid surfactants, polyethylene glycol lauryl ether and sarcosinates which aid the production of foam without the use of a synthetic propellant,
G) water, and
H) optionally one or more water-soluble substances,
with the proviso that the water content of the emulsion is ≥70% by weight and the content of surfactant (F) is from 0.01 to less than 10% by weight, based on the weight of the total emulsion;
with the proviso that the oil-in water emulsion does not contain a propellant gas; and
wherein the foam contains ambient air and does not contain a synthetic gas mixture;
wherein the emulsifier A) is an emulsifier mixture A1) consisting of:
a) at least one nonionic primary emulsifier, and
b) at least one secondary emulsifier containing one or more acid functions and whose acid function is optionally completely or partially neutralized;
wherein the primary nonionic emulsifier component (a) comprises one or more polyglycerol laurates or mixtures of polyglycerol laurates with one or more sorbitan laurates.

* * * * *